US010456925B2

(12) United States Patent
Paavilainen et al.

(10) Patent No.: US 10,456,925 B2
(45) Date of Patent: Oct. 29, 2019

(54) GRIPPER FINGER AND GRIPPER

(71) Applicant: Thermo Fisher Scientific Oy, Vantaa (FI)

(72) Inventors: Sami Paavilainen, Vantaa (FI); Juha Savonsalmi, Vantaa (FI)

(73) Assignee: Thermo Fisher Scientific Oy, Vantaa (FI)

( * ) Notice: Subject to any disclaimer, the term of this patent is extended or adjusted under 35 U.S.C. 154(b) by 0 days.

(21) Appl. No.: 15/771,447

(22) PCT Filed: Oct. 28, 2016

(86) PCT No.: PCT/FI2016/050757
§ 371 (c)(1),
(2) Date: Apr. 27, 2018

(87) PCT Pub. No.: WO2017/072414
PCT Pub. Date: May 4, 2017

(65) Prior Publication Data
US 2018/0311828 A1    Nov. 1, 2018

(30) Foreign Application Priority Data
Oct. 30, 2015   (FI) ..................................... 20155777

(51) Int. Cl.
*B25J 15/00*       (2006.01)
*B25J 19/02*       (2006.01)
*G01N 35/00*       (2006.01)

(52) U.S. Cl.
CPC ......... *B25J 15/0033* (2013.01); *B25J 19/025* (2013.01); *G01N 35/0099* (2013.01)

(58) Field of Classification Search
CPC ................ B25J 15/0033; B25J 15/0042; B25J 15/0253; B25J 15/0293; B25J 19/025; G01N 35/0099; Y10S 901/39; Y10S 901/46; Y10S 901/47
USPC ....................................... 294/119.1, 207, 907
See application file for complete search history.

(56) References Cited

U.S. PATENT DOCUMENTS

| 5,605,218 | A   | 2/1997  | Von Froreich |
|-----------|-----|---------|--------------|
| 6,264,419 | B1* | 7/2001  | Schinzel .................. B25J 9/023 294/119.1 |
| 6,435,582 | B1  | 8/2002  | Dasilva et al. |
| 6,520,313 | B1  | 2/2003  | Kaarakainen et al. |
| 8,439,414 | B2* | 5/2013  | Neeper .................... B25J 9/102 294/119.1 |

(Continued)

FOREIGN PATENT DOCUMENTS

| JP | 20030083985 A | 3/2003 |
| WO | WO2004013640 A1 | 2/2004 |

(Continued)

*Primary Examiner* — Dean J Kramer
(74) *Attorney, Agent, or Firm* — Seppo Laine Oy (57) ABSTRACT

A gripper comprising an actuator and two fingers mounted parallel at a distance from each other on the actuator for movement perpendicularly to a longitudinal axis of the fingers, the fingers having a longitudinal body attached at one end to the actuator. The fingers having two longitudinal claws at the end opposite to the end attached to the actuator, the claws being spaced apart so that there is an elongated gap between the claws. At least one of the fingers having a groove for accommodating an optical fiber which extends partially into the elongated gap.

12 Claims, 7 Drawing Sheets

(56) References Cited

U.S. PATENT DOCUMENTS

| | | | |
|---|---|---|---|
| 9,016,743 B2* | 4/2015 | Itoh | G01N 35/0099 |
| | | | 294/106 |
| 2003/0223916 A1 | 12/2003 | Testrut et al. | |
| 2004/0074320 A1 | 4/2004 | Itoh | |
| 2010/0028124 A1 | 2/2010 | Lackner et al. | |
| 2010/0066109 A1 | 3/2010 | Pedrazzini | |
| 2012/0134769 A1* | 5/2012 | Friedman | G01N 35/0099 |
| | | | 414/751.1 |
| 2012/0177473 A1 | 7/2012 | Smith | |
| 2013/0309057 A1 | 11/2013 | Yasuda et al. | |
| 2014/0005829 A1 | 1/2014 | Chhatpar et al. | |
| 2014/0036276 A1 | 2/2014 | Gross et al. | |
| 2014/0102239 A1* | 4/2014 | Umeno | B25J 15/0033 |
| | | | 74/490.01 |

FOREIGN PATENT DOCUMENTS

| | | |
|---|---|---|
| WO | WO2008067846 A1 | 6/2008 |
| WO | WO2011017586 A1 | 2/2011 |
| WO | WO2012129110 A1 | 9/2012 |

\* cited by examiner

GRIPPER FINGER AND GRIPPER

FIELD

The invention relates to grippers for manipulating or transferring test tubes in laboratories. Especially the invention relates to a finger of such gripper.

BACKGROUND

The invention relates to the field of clinical laboratory automation where coded sample vessels and tubes are transferred automatically from one analysis station to another. The system needs to be able to read the tube coding information in each of the transfer phases so that samples are handled correctly and errors are minimized.

When a sample, for example a blood sample, is withdrawn from a patient into a sample or test tube, all the sample tubes used are coded with sample and patient information. The coding is generally provided in the form of a one or two dimensional barcode on a sticker which the analyst attaches to the side of the sample tube. The coding contains information on the sample and analyses to be performed on the sample. All this information between the automated sample transfer and handling system and the analyzers is collectively coordinated by the laboratory information system (LIS).

A commercial or a hospital clinical laboratory handles thousands of samples a day. It is of utmost importance that all errors in the process are minimized and the system operates reliably and smoothly. Usually sample tubes are placed on carriers moving along a track operating between the various analysis stations. The LIMS system instructs the system to convey the sample tubes to correct analyzers (analysis stations) according to the information given in the sample tube bar code and/or carrier RFID chip. Details between different systems vary, but in general there are code reading positions along the track and at every line cross sections so that the sample tubes are directed on a correct route. An example of such a system may be found in U.S. Pat. No. 5,605,218 or 6,520,313.

There are occasions in the process when the data is only read from the sample tubes, for example when the samples are moved from sampling laboratory or cold storage to automated transport and analysing system. The sample tubes are lifted with a gripper. The gripper moves down vertically to grab the tube from its cap and/or upper sidewalls. The attachment of the gripper claws and/or fingers against the tube must be secure but not too tight to break the tube. The tube is transferred horizontally to the receiving position and the gripper moves the tube down and releases the tube by opening up the claws when the tube sits securely in its place.

One type of gripper comprises two elongate gripping fingers and an actuator for moving the fingers in relation to each other. The fingers are in upright position and the movement occurs in perpendicular direction in relation to the longitudinal dimension of the fingers. The actuator may operate on pressurized air, electrically, by magnets or by any common actuating means. Such actuators are readily available and they can be equipped with suitable type of fingers for gripping the articles that are handled.

One problem related to the above described grippers is possible errors in reading the bar code on sample tubes. As the bar codes are attached to sample tubes manually and they may be quite long, the sticker with the bar code may reach close to the cap or mouth of the sample tube. In such case the fingers of the sample tube may extend over the bar code. If the bar code is partially covered by the finger, the bar code can't be read reliably. This problem has been solved by returning the sample tube to picking point, releasing the grip and rotating the gripper of tube whereafter the code is read again. This slows the process down. Slowing of the process decreased productivity but a more severe problem is danger of deterioration of samples that must be analysed and treated rapidly. Another possibility is to use a gripper having three or more thin fingers. A problem with multiple fingers is that mechanisms for moving multiple fingers are quite complicated.

SUMMARY OF THE INVENTION

The invention is defined by the features of the independent claims. Some specific embodiments are defined in the dependent claims.

According to a first aspect of the present invention, there is provided a finger for a gripper, the finger comprising a longitudinal body, means for attaching the body to an actuator and two longitudinal claws at the end opposite to the means of attachment, the claws being spaced apart so that there is an elongate longitudinal gap between the claws.

According to a second aspect of the present invention, there is provided a gripper comprising an actuator and two parallel fingers mounted parallel at a distance from each other on the actuator for movement perpendicularly to a longitudinal axis of the fingers, the fingers comprising a longitudinal body part, means for attaching the body to the actuator and two longitudinal claws at the end opposite to the means of attachment, the claws being spaced apart so that there is an elongate longitudinal gap between the claws.

According to one aspect of one embodiment of the invention, at least one finger comprises an optical fibre placed between the claws of the finger.

EMBODIMENTS

Definitions

In the present context, the term "actuator" comprises apparatuses for providing translational linear movement between two bodies in relation to each other. The driving force may be pressurized fluid, electricity, magnetism or similar force.

Means for attachment includes but is not limited to screws, snap on attachments, welding, glue, rivets and bayonets, for example.

Bar code is an array of parallel rectangular bars and spaces that creates a symbology representing a number or alphanumeric identifier.

Quiet zone in automation is a white blank space on a bar code immediately preceding the first bar and immediately following the last bar.

Figure 1:
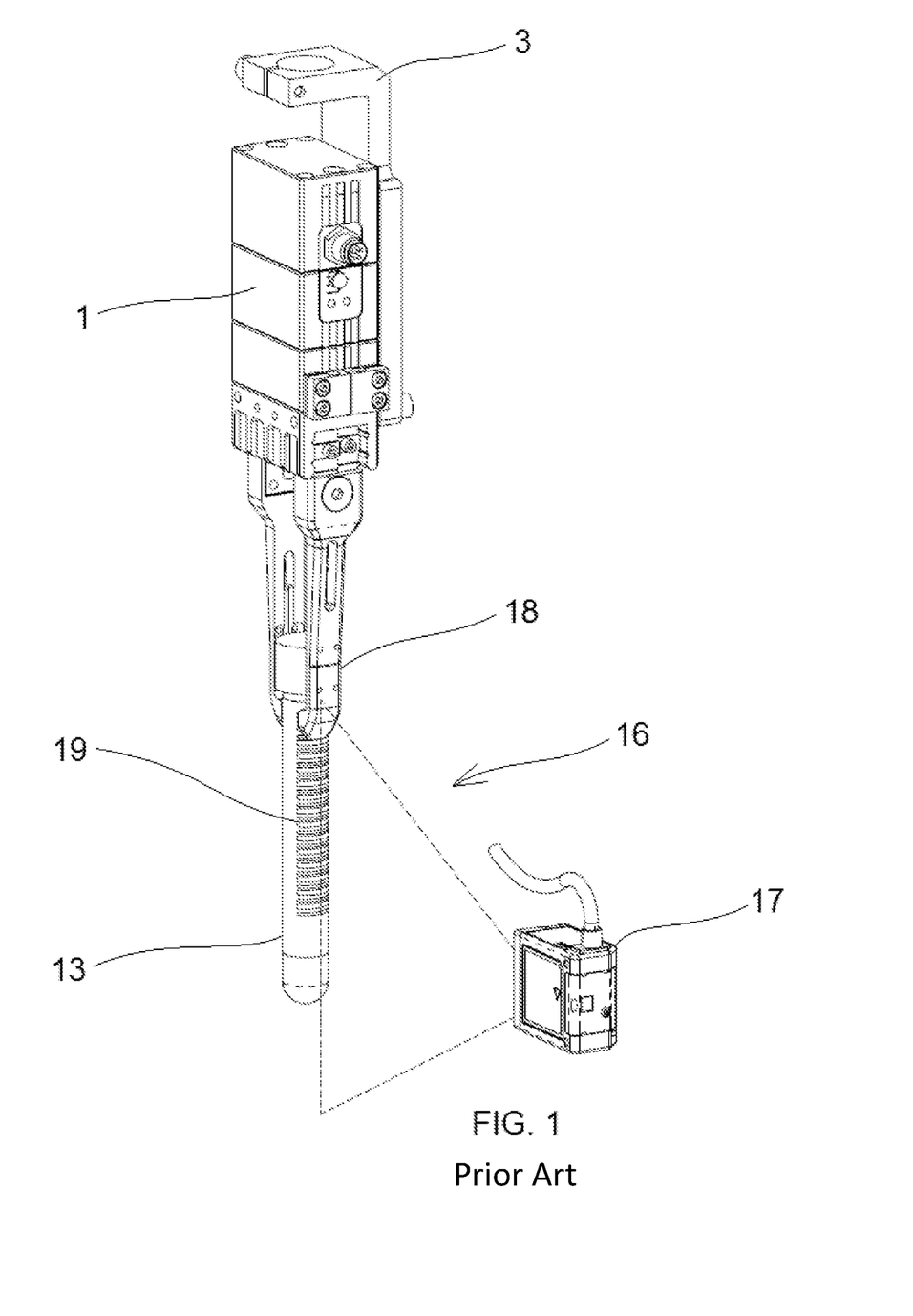
FIG. 1 illustrates a known gripper.
Figure 2:
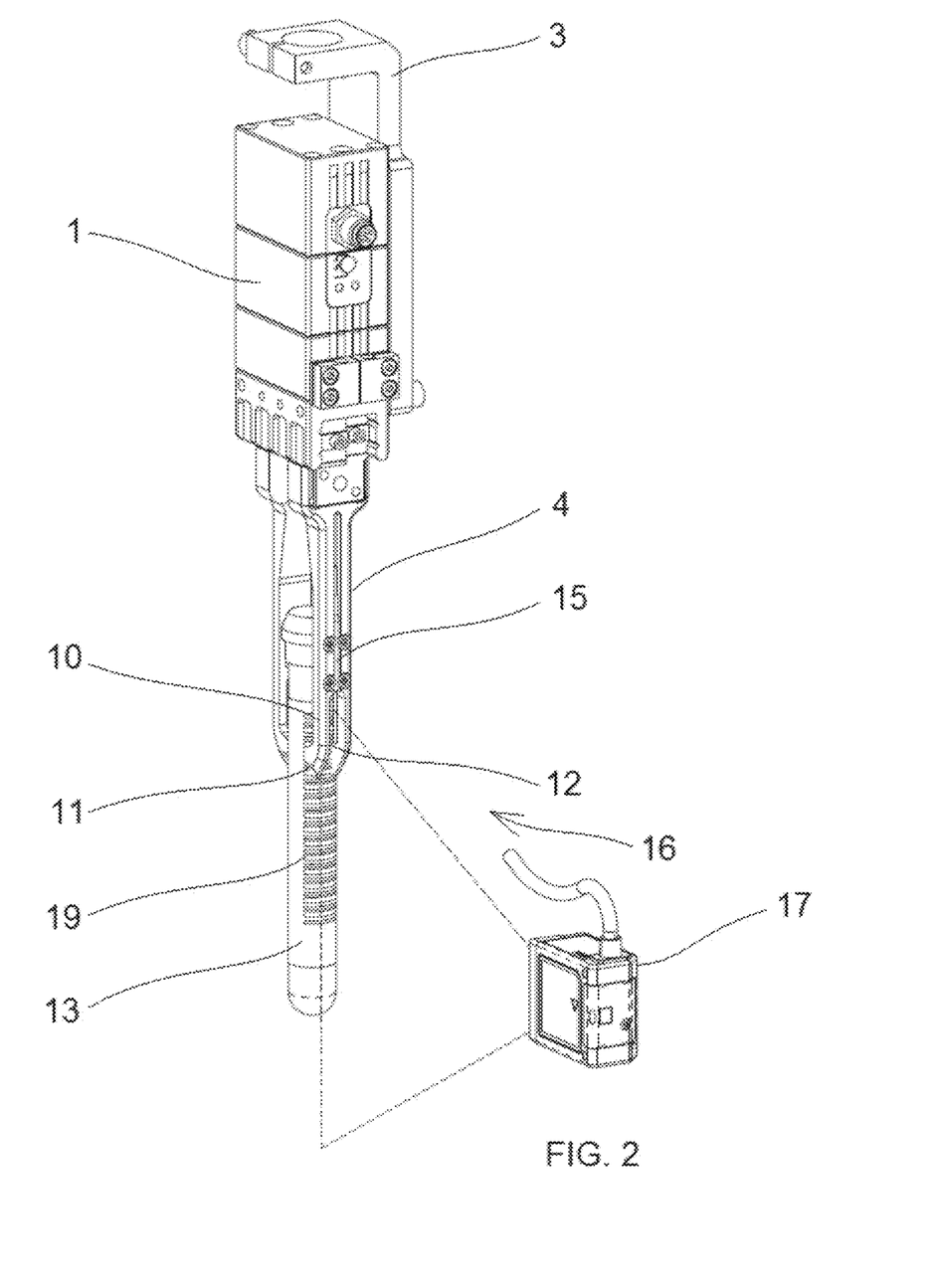
FIG. 2 illustrates a gripper according to at least some embodiments of the invention.
Figure 3:
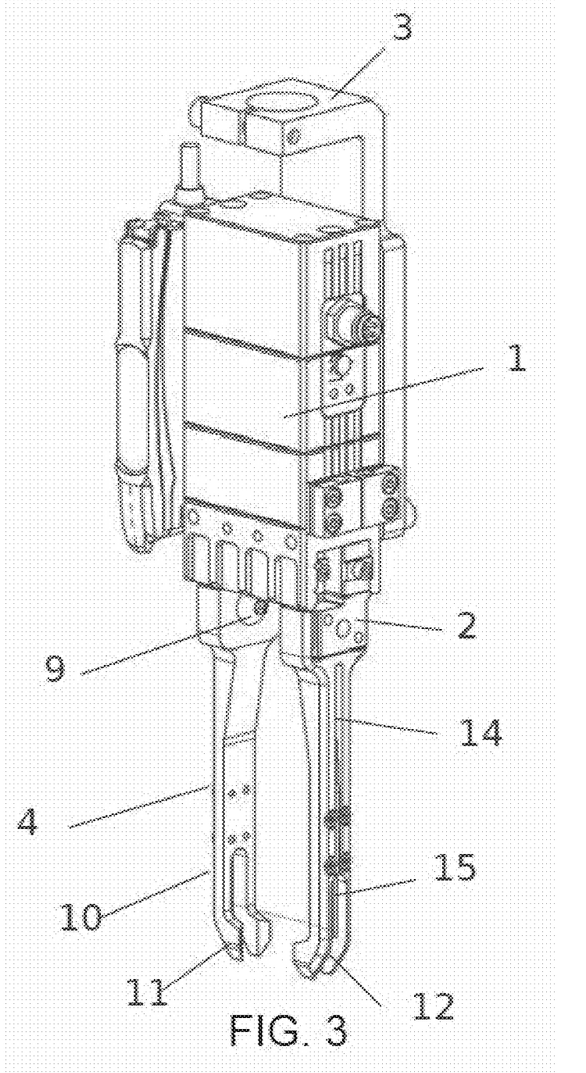
FIG. 3 illustrates a gripper in accordance with at least some embodiments of the present invention.
Figure 4:
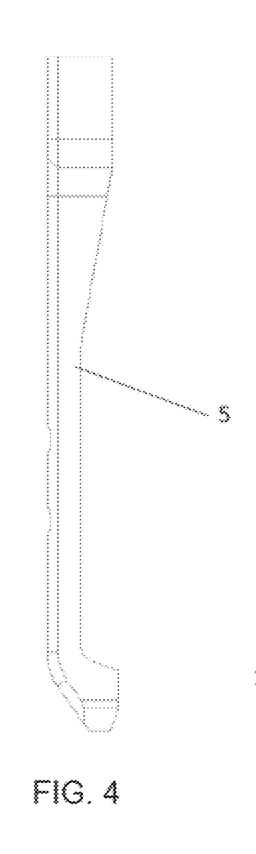
FIGS. 4-6 illustrate an example of one embodiment of the finger according to the invention.

FIG. 1 shows a known gripper 1 gripping a sample tube 13. The known finger 18 has gripped the sample tube 13 at the place of the bar code 19. As can be seen from the drawing, the known finger 18 now covers partly the bar code rendering it unreadable. The known finger 18 intersects the beam of the bar code reader 17 as illustrated in FIG. 1. In this situation the test tube has to be released and the gripper of tube 13 rotated so that new gripping position that doesn't cover the bar code 19 is obtained. As the location of the bar code in relation to the known fingers 18 of the gripper 1 is not known, it may be necessary to repeat gripping of the sample tube even more than two times. This obviously increases the handling time of the sample tubes 13 considerably.

The above situation can be avoided by using a gripper according to at least one embodiment of the invention. According to the invention, the finger 4 of the gripper 1 is provided by a gap 12 that divides the finger 4 into at least two claws 11. Now the bar code is always sufficiently visible for the beam of the bar code reader 17 and reliable reading to the code 19 is possible. The gap 12 may be dimensioned to accommodate an optical fibre 15 that enables detection of the presence of the sample tube. The various embodiments of the invention are described in more detail in the following text.

The idea of the invention is to provide a gripper having two gripping fingers that decrease reading errors when a test tube with a bar code is held with the gripper when the bar code is read. Both fingers of the gripper have an end with two claws with an elongate gap between the claws. The gap permits reading the bar code between the claws while the claws hold a sample tube. The bar code reading can be performed according to basic methods in the art. FIG. 1 illustrates a gripper in accordance with at least some embodiments of the present invention. The main body of the gripper is formed of an actuator 1. In this example the actuator 1 is an electric actuator having two mounting tabs 2 that are opposite to each other. The tabs 2 are at a distance from each other and can be made to move closer to each other and back so that a closed and open position is obtained. This movement is used to provide a gripping action and releasing action needed to operate the gripper. Electricity is used to cause the moving force. The gripper can be mounted to a manipulator or a robotic arm by a mounting bar 3. The manipulator is used to perform horizontal, vertical and rotational movements needed for transferring the gripper and a sample tube held by it.

The gripper has two identical fingers for gripping a sample tube. The finger 4 is an elongate fork-like part that comprises an elongate body 5 having a recess 6 at one end. In here the recess is mainly a rectangular cut extending inwards from the end of the finger 4. In the recess there is one large hole 7 and two smaller holes 8. The recess 6 is formed to accommodate the protruding end of the tab 2 of the actuator. The holes 7, 8 are used to secure the finger 4 on the end of the tab 2 by screws 9. As can be understood, the recess and locking elements like screw holes 7, 8 are designed according to the form and design of the end of the tab 2. At the end of the finger 4 opposite to the recess 6 are two claws 10. The claws 10 are symmetrical and have a hook at their end. The ends of the hooks 11 are formed to grip a tubular sample tube. The claws 11 are separated by an elongate gap 12 so that the claws are distanced from each other.

The gap 12 is most preferably at least 2 mm wide, preferably at least 5 mm wide but could be even 8 mm wide. The ultimate width of the fingers and thus of the claws and the gap between them depends naturally on the width of the sample tube to be gripped and the size of the bar code to be read. The claw must be narrower than the width of the bar code to enable the bar code reading. The gap 12 must also extend vertically so high that the bar code attached to side wall of the gripped sample tube is revealed entirely and the bar code reading can be performed successfully and reliably. According to one preferred embodiment of the gripper, the finger 4 height is 90 mm, claw 10 width is 10 mm, gap 12 width is 5 mm and gap 12 height is 25.5 mm. This design can be used for example Vacuette 6 ml 13×100 blood collection tubes. A minimum length of the gap is considered to be 15 mm, which allows reading of the bar code reliably. CLSI standards for bar codes usage in clinical laboratory systems define that the preferred symbology for use in a laboratory automation system is Code 128. It includes an inherent check character and is read bidirectionally.

Figure 6:
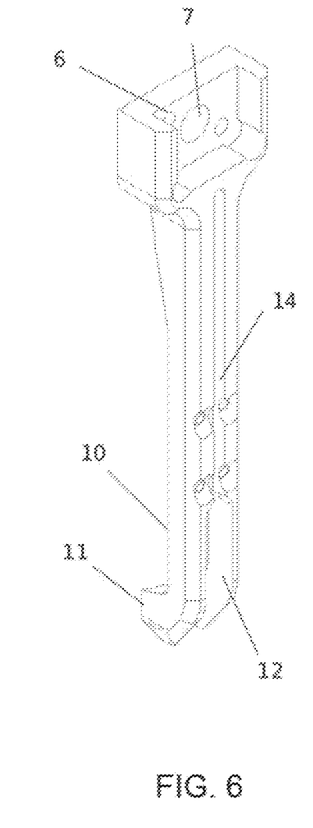
Figure 7:
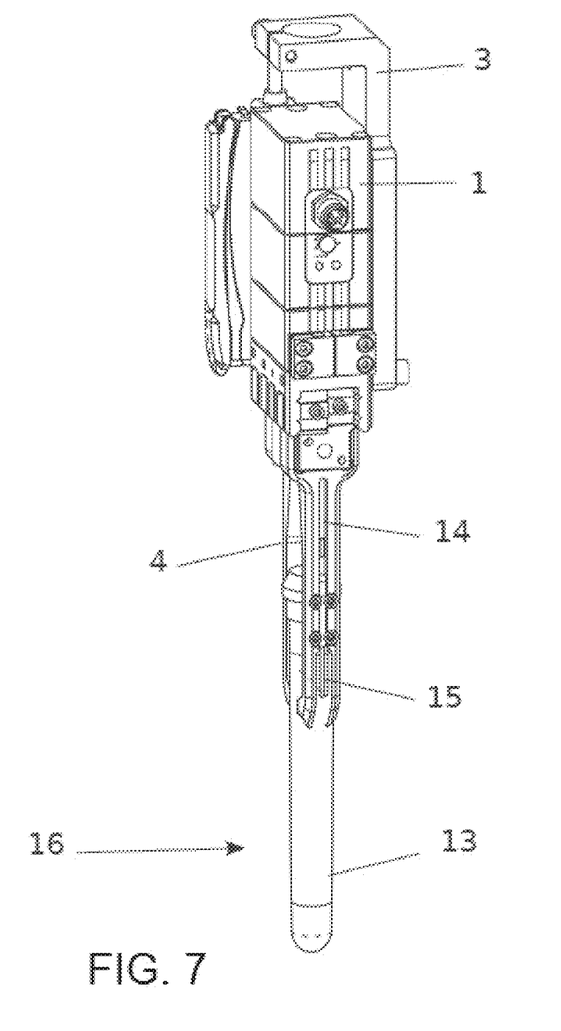
FIG. 7 illustrates the gripper of FIG. 1 gripping a sample tube.
Figure 8:
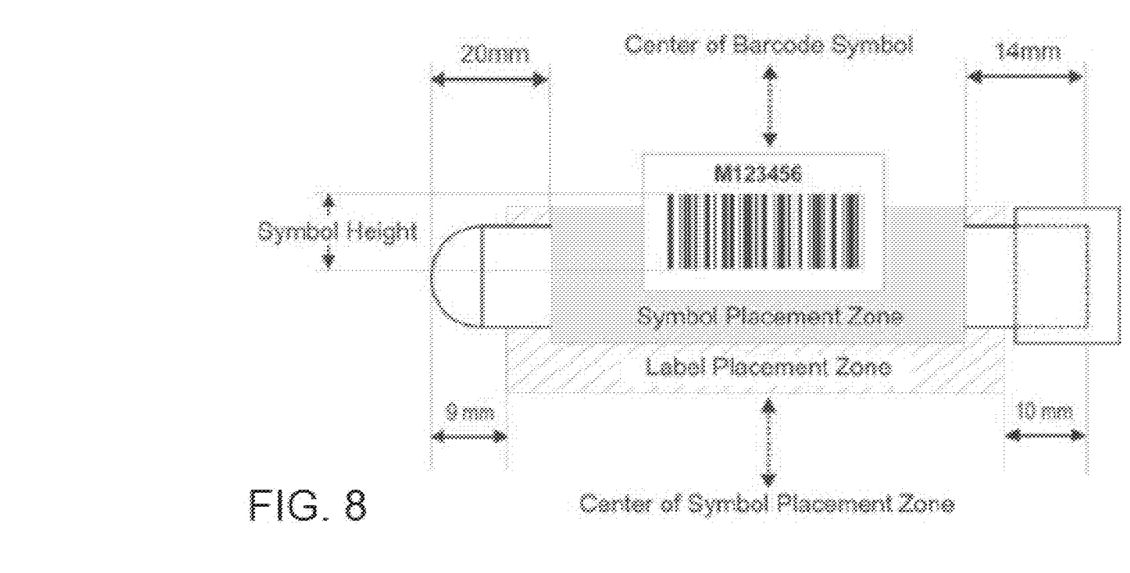
FIGS. 8 and 9 illustrate placement and dimensions of a bar code.
Figure 9:
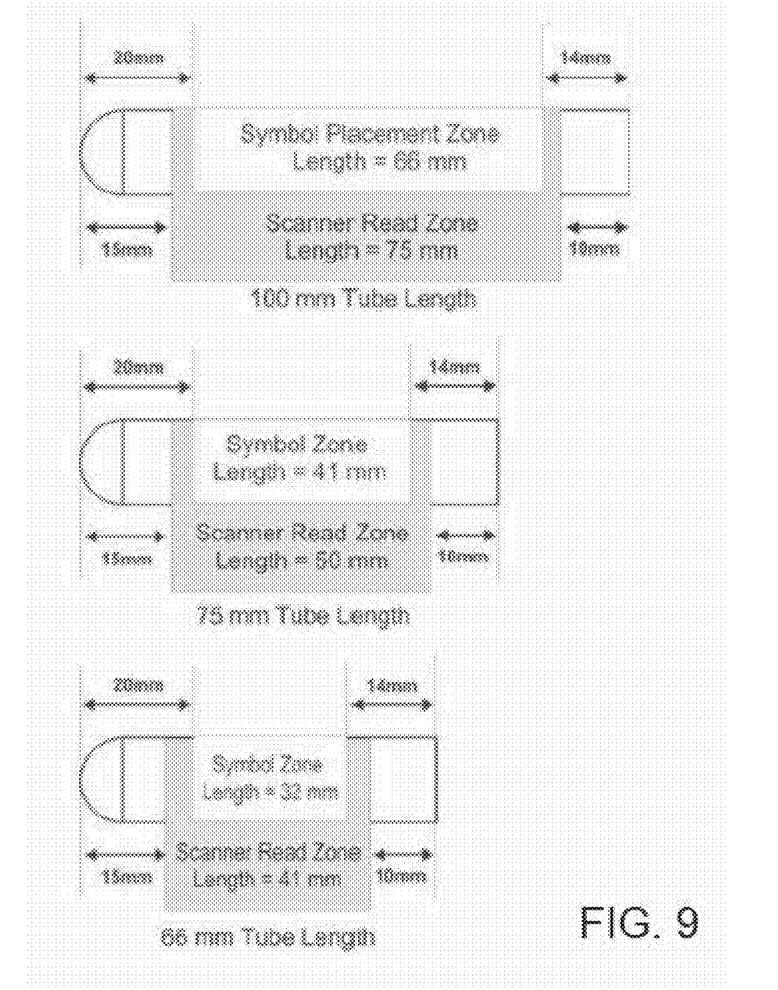

CLSI standards for bar codes usage in clinical laboratory systems also define that the bar code should be placed in the center of a symbol placement zone. The height of the bar code symbol on the sample tube is in maximum 10 mm. The symbol placement zone is the area 20 mm above the bottom of the tube to a distance 14 mm below the top of the tube, excluding the cap. The size of the placement zone varies depending on the length of the tube, see FIG. 6.

A minimum length of 10 mm from the end of bar code to the tube cap or 9 mm from the bottom of the tube has been set as a label in this area may prevent the specimen tube from being properly handled by robotic carriers. This also allows more latitude in the placement of the container in the carrier and permits the use of a higher skew.

The bar code label is advised to be applied as follows:

The label shall be placed with the bars perpendicular to the axis of the tube. The label skew shall be less than ±7.5% with respect to the axis of the specimen container.

The label shall be applied to the cylindrical portion of the tube below the rim, skirt or cap of the sample container. The label should be applied below the top 10 mm of the tube and above the bottom 9 mm of the tube.

A maximum of three labels is recommended (including the manufacturers label, if present) although there are times when four labels may be commonly used.

The label width must be 5 mm less than the circumference of the tube. This allows a window into the tube so that systems or humans can view the liquid level or quality of the sample.

The bar code itself has recommended and minimum widths, for narrow codes recommended being 0.191 mm and minimum 0.127 mm. Minimum width of the quiet zone must be at least ten times the minimum width of the bar. Recommendation for the quiet zone is 3.5 mm.

Some manufacturers use caps that extend about 10 mm downwards from the top of the sample tube. If a label is positioned as described above, the edge of the label is right below the edge of the cap. Now, when the sample tube is gripped, the fingers of the gripper cover inevitably part of the code making reading of it impossible. Splitting of the end of a finger makes reading of the label possible.

Figure 5:
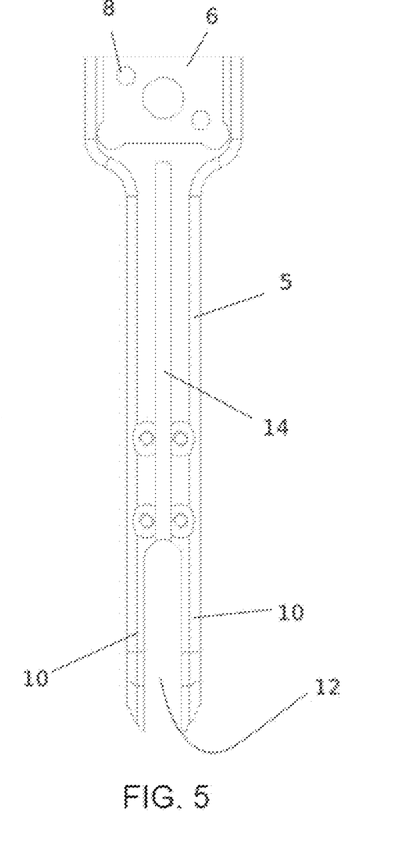

The finger 4 comprises a groove 14 that extends along a surface of the finger to the bottom of the gap 12. This groove 14 is used for leading an optical fibre to the gap between the claws. The optical fiber 15 is used to form an indicator for indicating presence of a test tube between the fingers 4. Typically the indicator comprises a light emitting optical fiber in one finger 4 and a light detecting optical fiber in other finger 4. The fibers extend partially along the gap 12. The diameter and the width of the gap is dimensioned so that the fiber 15 is thinner than the gap 12 and does not cover the width of the gap 12. So the bar code can be read between the edges of the claws and the fiber 15. The gripper grips sample tubes 13 by moving the fingers with the actuator closer to each other and releases the tube 13 by moving the fingers away from each other. When fingers are moved to closed gripping position, the ends of the hooks 11 are pressed against a sample tube 13 (FIG. 5). Thereby four gripping points are formed and secure grip is obtained. When the bar code on the side 16 of the sample tube 13 is read, the gripper is rotated. Now if the code is partially covered by fingers 4, the code is still visible between the claws 10 and can be reliably read.

There are a number of finger-type grippers available. They have to be operable by actuators reliably so that each finger is moved identically and with identical force. For these reasons grippers with multiple fingers are mechanically difficult to make and difficult to operate. On the other hand grippers using two fingers should have broad enough contact points to provide solid grip and the contact point should be formed to accommodate the curved surfaces of sample tubes having various diameters.

Since the sample tubes are placed randomly in their racks, the bar code that is placed on a specific place along the surface of the tube and directed parallel to the vertical central axis of the tube may be positioned in any direction rotationally. In order to read the code the tube is rotated in the gripper so that the code is positioned towards the code reader in some rotational position of the gripper and tube and is readable.

If the bar code on the tube reaches too high on the tube close its upper edge or mouth or cap, the fingers of the gripper may cover the bar code on that tube end and the code cannot be read reliably. This problem is mostly avoided by using a gripper having two fingers that are split at the lower (distal from the mounting end) ends so that a gap remains between the claws so formed. The gap allows the bar code to be read entirely as a part of the code is always visible for reading as long as the code is made wider than the claw and the gap is high enough to extend to the end of the bar code at the cap end's side of the tube. The bar codes are standardized and have a definite width. The arrangement reduces reading errors considerably. In a test series the number of misreadings was reduced from about 2 to 3 percent to 0.01 percent. The arrangement also allows using a thin optical fibre in the gap between the claws. Using two fingers keeps the actuator simple and easily operable. Splitting the fingers into two claws brings also stability and reliability to the grip as four gripping points separated from each other are provided.

The reading of the bar code on a sample tube using a gripper described above comprises the following steps:
gripping the upper portion of a sample tube with a bar code on its side wall with said gripper,
moving the gripper and the sample tube to a bar code reading position,
rotating the gripper and the sample tube,
reading the bar code attached to the sample tube side wall through a gap between the claws of a finger of the gripper,
sending the information to a laboratory information system, and
moving the gripper and the sample tube to the same or to a second position and releasing the sample tube from the gripper.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

Reference throughout this specification to one embodiment or an embodiment means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. Where reference is made to a numerical value using a term such as, for example, about or substantially, the exact numerical value is also disclosed.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. In addition, various embodiments and example of the present invention may be referred to herein along with alternatives for the various components thereof. It is understood that such embodiments, examples, and alternatives are not to be construed as de facto equivalents of one another, but are to be considered as separate and autonomous representations of the present invention.

Furthermore, the described features, structures, or characteristics may be combined in any suitable manner in one or more embodiments. In the description, numerous specific details are provided, such as examples of lengths, widths, shapes, etc., to provide a thorough understanding of embodiments of the invention. One skilled in the relevant art will recognize, however, that the invention can be practiced without one or more of the specific details, or with other methods, components, materials, etc. In other instances, well-known structures, materials, or operations are not shown or described in detail to avoid obscuring aspects of the invention.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

The verbs "to comprise" and "to include" are used in this document as open limitations that neither exclude nor require the existence of also un-recited features. The features recited in depending claims are mutually freely combinable unless otherwise explicitly stated. Furthermore, it is to be understood that the use of "a" or "an", that is, a singular form, throughout this document does not exclude a plurality.

INDUSTRIAL APPLICABILITY

At least some embodiments of the present invention find industrial application in clinical laboratory automation.

REFERENCE SIGNS LIST

| No | Definition |
|---|---|
| 1 | actuator |
| 2 | tab |
| 3 | mounting bar |
| 4 | finger |
| 5 | body of finger |
| 6 | recess |
| 7 | hole |
| 8 | hole |
| 9 | screw |
| 10 | claw |
| 11 | hook |
| 12 | gap |
| 13 | sample tube |
| 14 | groove |
| 15 | optical fibre |
| 16 | side of sampletube |
| 17 | bar code reader |
| 18 | known finger |
| 19 | bar code |

The invention claimed is:

1. A finger for a gripper, comprising:
   an optical fiber,
   a longitudinal body, means for attaching the body to an actuator and two longitudinal claws at the end opposite to the means for attachment, the claws being spaced apart so that there is an elongated gap between the claws, and
   a groove on the surface of the finger for accommodating the optical fiber, wherein the optical fiber extends partially into the elongated gap.

2. The finger according to claim 1, wherein the gap is at least 2 mm wide.

3. The finger according to claim 1, wherein the length of the gap is at least 15 mm.

4. The finger according to claim 1, wherein the width of each claw is narrower than a bar code.

5. The finger according to the claim 1, wherein the gap extends at least to the upper edge of a bar code on a sample tube when attached to the sample tube.

6. The finger according to claim 1, wherein the width of the gap is within the range of 2-8 mm.

7. The finger according to claim 1, wherein the length of the gap is at least 25.5 mm.

8. The finger according to claim 1, wherein the diameter of the optical fiber is thinner than the width of the gap.

9. A gripper comprising an actuator and two fingers mounted parallel at a distance from each other on the actuator for movement perpendicularly to a longitudinal axis of the fingers, the fingers comprising a longitudinal body, means for attaching the body to the actuator and two longitudinal claws at the end opposite to the means of attachment, the claws being spaced apart so that there is an elongated gap between the claws, wherein at least one finger has at least one groove on its surface for accommodating an optical fiber, further comprising at least one optical fiber mounted on the at least one groove and extending partially into the elongated gap between the claws.

10. The gripper according to claim 9, wherein the diameter of the optical fiber is smaller than the width of the gap between the claws.

11. The gripper according to claim 10, wherein the gap is at least 2 mm wide.

12. A method of reading a bar code on a sample tube using a gripper comprising the following steps:
   gripping the upper portion of a sample tube with a bar code on its side wall with said gripper,
   moving the gripper and the sample tube to a bar code reading position,
   rotating the gripper and the sample tube,
   reading the bar code attached to the sample tube side wall through a gap between claws of a finger of the gripper,
   moving the gripper and the sample tube to the same or to a second position, and,
   releasing the sample tube from the gripper,
   the gripper comprising an actuator and two fingers mounted parallel at a distance from each other on the actuator for movement perpendicularly to a longitudinal axis of the fingers, the fingers comprising a longitudinal body, means for attaching the body to the actuator and two longitudinal claws at the end opposite to the means of attachment, the claws being spaced apart so that there is an elongated gap between the claws, wherein at least one finger has at least one groove on its surface for accommodating an optical fiber, said optical fiber extending at least partially into the elongated gap.

* * * * *